United States Patent [19]

Okamura et al.

[11] 4,264,512

[45] Apr. 28, 1981

[54] 3-DEOXY-1α-HYDROXY- AND 3-DEOXY-1α,25-DIHYDROXYCHOLECAL-CIFEROL AND PROCESSES FOR THE PREPARATION THEREOF

[75] Inventors: William H. Okamura; Anthony W. Norman; Manindra N. Mitra, all of Riverside, Calif.

[73] Assignee: Regents of the University of California, Berkeley, Calif.

[21] Appl. No.: 750,590

[22] Filed: Dec. 15, 1976

Related U.S. Application Data

[63] Continuation of Ser. No. 617,768, Sep. 29, 1975, which is a continuation-in-part of Ser. No. 567,442, Apr. 11, 1975.

[51] Int. Cl.³ .............................................. C07J 9/00
[52] U.S. Cl. ........................ 260/397.2; 260/239.55 R
[58] Field of Search ...................................... 260/397.2

[56] References Cited

U.S. PATENT DOCUMENTS

| 3,822,254 | 7/1974 | Partridge, Jr. et al. | 260/397.2 |
| 3,836,527 | 9/1974 | Irmscher et al. | 260/239.55 A |
| 3,887,545 | 6/1975 | Iacobelli et al. | 260/397.2 |

*Primary Examiner*—Elbert L. Roberts
*Attorney, Agent, or Firm*—Stevens, Davis, Miller & Mosher

[57] ABSTRACT

Processes for the preparation of 3-deoxy-1α-hydroxy-cholecalciferol and 3-deoxy-1α,25-dihydroxycholecalciferol, novel analogs of cholecalciferol possessing potent intestinal calcium transport stimulatory activity without significant concomitant bone calcium mobilizing activity, are disclosed.

14 Claims, No Drawings

3-DEOXY-1α-HYDROXY- AND 3-DEOXY-1α,25-DIHYDROXYCHOLECALCIFEROL AND PROCESSES FOR THE PREPARATION THEREOF

This is a continuation of application Ser. No. 617,768 filed Sept. 29, 1975 which in turn is a continuation-in-part of application Ser. No. 567,442, filed Apr. 11, 1975.

The invention described herein was made in the performance of work under research grants from the United States Public Health Service.

BACKGROUND OF THE INVENTION

As a result of extensive investigation performed over the past several decades, various metabolites and analogs of vitamin D have been isolated and prepared. For example, metabolites, such as 25-hydroxycholecalciferol and 1α,25-dihydroxycholecalciferol, have been isolated from liver and kidney homogenates, respectively, and analogs, such as 1α-hydroxycholecalciferol, have been prepared from natural sources. Vitamin D and its known metabolites and analogs stimulate intestinal calcium transport and mobilize bone calcium with varying degrees of efficacy depending upon the degree and position of hydroxylation of the vitamin D molecule, but with virtually no separation of activity. Vitamin D and its known metabolites and analogs are potent intestinal calcium transport stimulators and potent bone calcium mobilizers.

Also as a result of these investigations, it has been established that vitamin D and its metabolites are hydroxylated at the 1α-position by the kidney and that 1α-hydroxylation is essential for biological activity in anepheric animals and man.

This subject is thoroughly reviewed by DeLuca, et al. in Physiological Reviews, 53, 327 (1973).

Potent vitamin D analogs selectively stimulating intestinal calcium transport without significantly mobilizing bone calcium would be highly desirable additions to the physicians's arsenal of drugs for the treatment of certain vitamin D metabolic disorders, such as osteoporosis. For the treatment of a wide spectrum of vitamin D related diseases associated with kidney failure or chronic uremia, potent vitamin D analogs bearing the key 1α-hydroxyl group eliminating the necessity for renal metabolism would also be highly desirable additions.

DETAILED DESCRIPTION OF THE INVENTION

The present invention relates to 3-deoxy-1α-hydroxycholecalciferol 13,

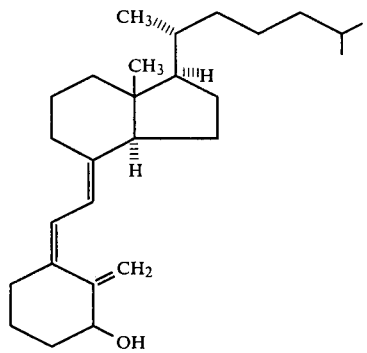

and 3-deoxy-1α,25-dihydroxycholecalciferol 13a

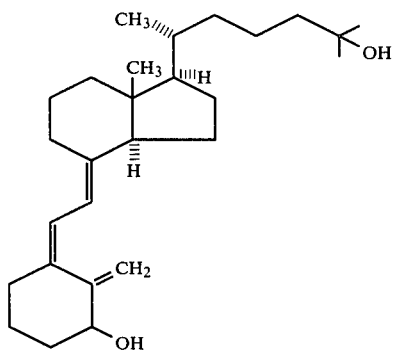

novel analogs of vitamin D bearing the necessary 1α-hydroxyl group and possessing the unique characteristic of stimulating intestinal calcium transport without significantly mobilizing bone calcium.

The present invention also relates to novel processes for the preparation of 3-deoxy-1α-hydroxycholecalciferol 13 starting from cholesterol 2. More particularly, the present invention relates to processes for the preparation of 3-deoxy-1α-hydroxycholecalciferol 13 comprising the steps of converting cholesterol 2 to 1α,2α-oxido-4,6-cholestadien-3-one 1, reductively cleaving 1α,2α-oxido-4,6-cholestadien-3-one 1 to 4,6-cholestadien-1α,3β-diol 4, selectively hydrogenolyzing 4,6-cholestadien-1α,3β-diol 4 to 1α-hydroxy-5-cholestene 5 and transforming 1α-hydroxy-5-cholestene 5 to 3-deoxy-1α-hydroxycholecalciferol 13, or alternatively, reductively cleaving 1α,2α-oxido-4,6-cholestadien-3-one 1 to 1α-hydroxycholesterol 6, selectively sulfonating 1α-hydroxycholesterol 6 to 1α-hydroxycholesteryl sulfonate 7 and reducing 1α-hydroxycholesteryl sulfonate 7 to 1α-hydroxy-5-cholestene 5.

In addition the present invention also relates to a novel process for the preparation of 3-deoxy-1α-25,dihydroxycholecalciferol 13a starting from cholesterol 2. More particularly, the present invention relates to a process for the preparation of 3-deoxy-1α,25-dihydroxycholecalciferol 13a comprising the steps of selectively sulfonating 1α,25-dihydroxycholesterol 14 to 1α,25-dihydroxycholesteryl sulfonate 16, reducing 1α,25-dihydroxycholesteryl sulfonate 16 to 1α,25-dihydroxy-5-cholestene 17 and transforming 1α,25-dihydroxy-5-cholestene 17 to 3-deoxy-1α,25-dihydroxycholecalciferol 13a.

In the formulas presented herein, the various substituents are illustrated as joined to the steroid nucleus by one of three notations: a solid line (—) indicating a substituent which is in the β-orientation (i.e., above the plane of the molecule), a dotted line (-----) indicating a substituent which is in the α-orientation (i.e., below the plane of the molecule), or a wiggly line (∼) indicating a substituent which may be in the α- or β-orientation or may be a mixture of both forms. The formulas have all been drawn to show the compounds in their absolute stereochemical configurations. Since the starting materials are derived from naturally occurring materials, the final products exist in the single absolute configuration depicted herein. However, the processes of the present invention are intended to apply as well to the synthesis of steroids of the racemic series. Thus, one may begin the synthesis utilizing racemic starting materials to prepare racemic products. Optically active products can then be prepared by resolution of the racemic products utilized in the preparation thereof, as hereinafter described, by standard resolution techniques well-known in the art.

As used throughout the specification and appended claims, the term "alkyl" denotes a straight or branched chain saturated hydrocarbon radical having 1 to 8 carbon atoms, such as, for example, methyl, 2-propyl, 2-methylpropyl, 3-methylpentyl, octyl and the like; the term "alkylphenyl" denotes a group mono- or polysubstituted by alkyl, such as, for example, tolyl, xylyl, mesityl and the like; the term "alkanoyl" denotes a radical derived by abstraction of the hydroxyl group from an alkylcarboxylic acid having 2 to 8 carbon atoms, such as acetyl, 2-methylpropionyl, 2-methylpentanoyl, octanoyl and the like; the term "alkanol" denotes an alcohol derived by combination of alkyl and hydroxyl radicals, such as, for example, methanol, 2-propanol, 2-methylpropanol, 3-methylpentanol, octanol and the like; the term "alkoxy" denotes a radical derived by abstraction of the hydroxyl proton from an alkanol, such as, for example, methoxy, 2-propoxy, 2-methylpropoxy, 3-methylpentoxy, octoxy and the like; and the term "halide" denotes chloride and bromide. The term "lower" refers to the numerical range 1 to 8.

In the first step of the process of the present invention for the preparation of 3-deoxy-1α-hydroxycholecalciferol 13, 1α,2α-oxido-4,6-cholestadien-3-one 1,

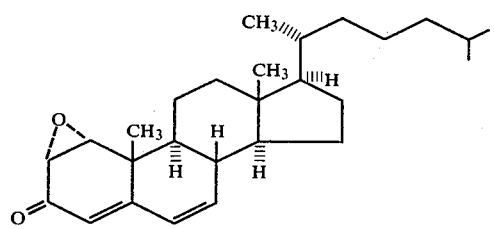

prepared by dehydrogenation of cholesterol 2

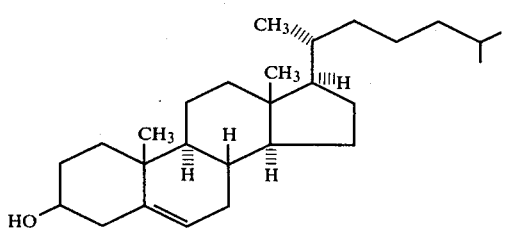

with 2,3-dichloro-5,6-dicyano-1,4benzoquinone to 1,4,6-cholestatrien-3-one 3

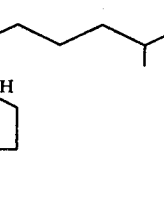

according to the procedure described by A. B. Turner (J. Chem. Soc. C, 2568 (1968)) followed by selective epoxidation of the 1,2-double bond with alkaline hydrogen peroxide according to the known procedure of B. Pelc and E. Kodicek (J. Chem. Soc. C, 1568 (1971)), is reduced to 4,6-cholestadien-1α,3β-diol 4.

The reduction of 1α,2α-oxido-4,6-cholestadien-3-one 1 is accomplished using a suitable aluminum hydride reducing agent suspended or dissolved in an inert organic solvent at a reaction temperature of up to about 50° C.

Among the suitable aluminum hydride reducing agents are alkali metal aluminum hydrides, such as lithium aluminum hydride and the like, alkali metal aluminum alkoxy hydrides, such as lithium tri-(tert.-butoxy)aluminum hydride, lithium diethoxyaluminum hydride and the like, and alkyl aluminum hydrides, such as diisobutylaluminum hydride and the like. Alkali metal aluminum hydrides are preferred; lithium aluminum hydride is most preferred.

Among the inert organic solvents are ethereal solvents, such as diethyl ether, diisopropyl ether, tetrahydrofuran, dioxane, 1,2-dimethoxyethane and the like, when alkali metal aluminum hydrides and alkali metal alkoxyaluminum hydrides are used as the reducing agents, and aromatic hydrocarbons, such as benzene, toluene, xylene and the like, when alkylaluminum hydrides are used as the reducing agents. Diethyl ether and tetrahydrofuran are the preferred ethereal solvents; diethyl ether is most preferred. Benzene and toluene are the preferred aromatic hydrocarbon solvents; toluene is most preferred.

While reaction temperatures below about 50° C. are not critical reaction temperatures above about 50° C. should be avoided to minimize possible hydrogenolysis of the 3β-hydroxyl group of the diendiol 4.

Similarly, the molar ratio of the aluminum hydride reducing agent to the diendiol 4 is not critical as long as the ratio is greater than 0.5. Molar ratios of about 1 to about 10 are preferred. A molar ratio of about 5 is most preferred.

In the second step of the process, the diendiol 4 is subjected to the conditions of the Birch reduction whereupon the 3β-hydroxyl group is hydrogenolyzed and the Δ⁴,⁶-diene system is conjugatively reduced to afford 1α-hydroxy-5-cholestene 5.

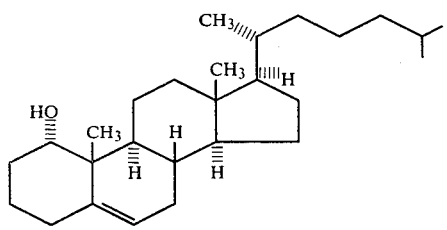

The reductive-hydrogenolysis of the diendiol 4 is effected by a solution of an alkali metal in a suitable ammoniacal solvent containing an appropriate inert organic cosolvent under an inert atmosphere at a temperature of about −33° to about 25° C.

Included among the alkali metals are sodium, potassium, lithium and the like. Sodium and lithium are preferred; lithium is most preferred.

Suitable ammoniacal solvents include ammonia and primary and secondary amines, such as methylamine, ethylamine, dimethylamine and the like. Ammonia and methylamine are preferred; ammonia is most preferred.

Among inert organic cosolvents are ethereal cosolvents, such as diethyl ether, tetrahydrofuran, dioxane and the like. Diethyl ether and tetrahydrofuran are preferred; tetrahydrofuran is most preferred.

Appropriate inert atmospheres include nitrogen, argon, helium and the like. Nitrogen and helium are preferred; nitrogen is most preferred.

While reaction temperatures within the range of about −33° to about 25° C. are not critical, the preferred reaction temperatures for reactions utilizing ammoniacal solvents boiling below about 25° C. are the boiling points of the solvents, and the preferred reaction temperatures for reactions utilizing ammoniacal solvents boiling above about 25° C. are about 25° C. The most preferred reaction temperature is the boiling point of ammonia, −33° C.

As in most Birch-type reductions, the molar ratio of the dissolving alkali metal to the diendiol 4 is not crucial. For the reduction of diendiol 4 to the enol 5, molar ratios within the range of about 25 to about 100 are preferred; molar ratios of about 50 are most preferred.

Alternatively, 1α-hydroxy-5-cholestene 5 may be prepared by reductive-cleavage of 1α,2α-oxido-4,6-cholestadien-3-one 1 to 1α-hydroxycholesterol 6

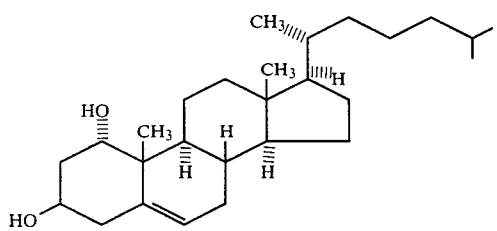

according to the procedure of Barton, et al. (J. Am. Chem. Soc., 95, 2748 (1973)) followed by selective sulfonation of the 3β-hydroxyl group of the endiol 6 to the sulfonate of formula 7

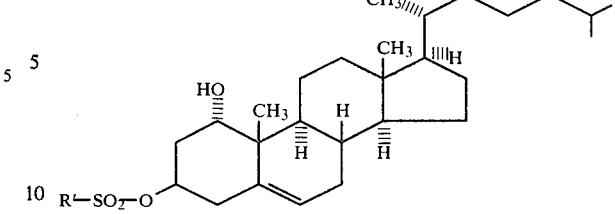

wherein R' is lower alkyl, phenyl or lower-alkylphenyl, and reduction of 7.

The selective sulfonation of the 3β-hydroxyl group of the endiol 6 is performed by treatment with about 1 to about 5 molar-equivalents of a sulfonyl halide of formual 8

$$R'-SO_2-X \qquad 8$$

wherein R' is lower alkyl, phenyl or lower-alkylphenyl and X is chloro or bromo,
in the presence of a basic solvent at a reaction temperature of about 0° C. to afford the sulfonate 7.

Among the basic solvents which have been found to be useful in the sulfonation step are trialkylamines, such as triethylamine, tripropylamine and the like, N,N-dialkylanilines, such as N,N-dimethylaniline and the like, and heteroaromatic amines, such as pyridine, and alkylpyridines, such as picolines, lutidines and collidines and the like. Preferred basic solvents are triethylamine and pyridine; pyridine is the most preferred basic solvent.

While the molar ratio of the sulfonyl halide 8 to the endiol 6 within the range of about 1 to about 5 is not crucial, a molar ratio of about 2 is preferred.

While reaction temperatures above about 0° C. are to be avoided to suppress disulfonate formation, i.e., sulfonation of the 1α- as well as the 3β-hydroxyl groups, a reaction temperature of about −10° C. is preferred.

Included among the preferred 3β-sulfonates of formula 7 are those compounds of formula 7 wherein R' is methyl, phenyl or 4-tolyl. The most preferred 3β-sulfonate of formula 7 is the compound of formula 7 wherein R' is 4-tolyl.

The last step of the alternative process for the preparation of 1α-hydroxy-5-cholestene 5, the reduction of a 3β-sulfonate of formula 7, is accomplished by dissolving a compound of formula 7 in an inert ethereal solvent, such as ether, dimethoxyethane, tetrahydrofuran, dioxane and the like, ether and tetrahydrofuran being preferred; ether being most preferred, and treating the solution with an alkali metal aluminum hydride, such as sodium aluminum hydride, lithium aluminum hydride and the like, lithium aluminum hydride being the preferred alkali metal aluminum hydride, at a temperature range from about 25° C. to the boiling point of the ethereal solvent, the boiling point of the inert ethereal solvent being the preferred reaction temperature.

The molar ratio of the alkali metal aluminum hydride to the sulfonate 7 is not critical. The reduction is conveniently carried out with a molar ratio of the reducing agent to the sulfonate 7 of about 1 to about 25, a molar ratio of about 10 being preferred.

In the next step of the process for the preparation of 3-deoxy-1α-hydroxycholecalciferol 13, 1α-hydroxy-5-cholestene 5 is converted to the acylate of formula 9

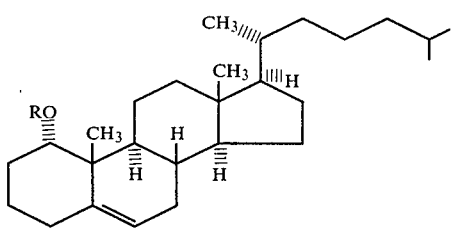

9

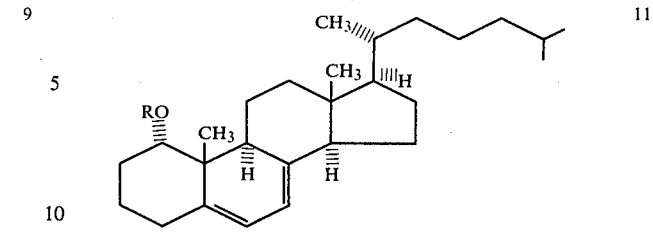

wherein R is lower alkanoyl, by means of acylating agents derived from straight or branched chain saturated alkanecarboxylic agents having 2 to 8 carbon atoms, such as alkanoyl halides and symmetrical alkanoic anhydrides, in the presence of a tertiary heteroaromatic amine, such as, for example, pyridine, picoline, lutidine, collidine and the like as the solvent system and acid-acceptor and N,N-dimethyl-4-aminopyridine as the catalyst at from about 15° C. to about the boiling point of the solvent system using from about 5 to about 20 moles of the acylating agent for each molar equivalent of 1α-hydroxy-5-cholestene 5. The acylation is preferably performed at about room temperature with about 10 moles of acylating agent for each mole of alcohol 9.

Suitable alkanoyl halides include acetyl halides, propionyl halides, 2-methylpropionyl halides, trimethylacetyl halides, hexanoyl halides, dimethylpentanoyl halides, octanoyl halides and the like; acetyl chloride, hexanoyl chloride and octanoyl chloride are preferred; acetyl chloride and octanoyl chloride are most preferred. Suitable symmetrical alkanoic anhydrides include acetic anhydride, proprionic anhydride, 2-methylpropionic anhydride, trimethylacetic anhydride, hexanoic anhydride, dimethylpentanoic anhydride, octanoic anhydride and the like; acetic anhydride, hexanoic anhydride and octanoic anhydride are preferred acetic anhydride and hexanoic anhydride are most preferred.

The subsequent steps of the process for the preparation of 3-deoxy-1α-hydroxycholecalciferol 13 are performed by utilizing procedures well-known in the art. Thus 1α-acyloxy-5-cholestene 9 is allylically brominated by means of 1,3-dibromo-5,5-dimethylhydanotoin in a suitable aromatic-aliphatic hydrocarbon solvent system, such as 1:1-benzene-hexane to a mixture of 7α- and 7β-bromo-1α-acyloxy-5-cholestenes of formula 10

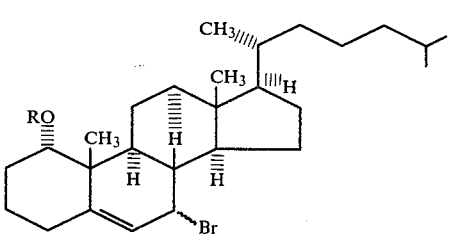

wherein R is as hereinbefore defined, which without further purification is dehydrobrominated by means of trimethylphosphite in an aromatic hydrocarbon solvent, such as xylene, to 1α-acyloxy-5,7-cholestadienes of formula 11 wherein R is as hereinbefore defined by procedures essentially the same as those employed by Barton, et al., supra for the synthesis of 1α,25-diacetoxy-7,8-dehydrocholesteryl acetate, and hydrolyzed to 1α-hydroxy-5,7-cholestadiene of formula 11 (wherein R is hydrogen) by means of an alkali metal hydroxide, such as sodium or potassium hydroxide and the like, dissolved in a suitable lower alkanol, such as methanol, ethanol and the like, at about room temperature under an inert atmosphere, such as nitrogen, helium and the like. The saponification of 1α-acyloxycholestane derivatives, such as compounds of formula 11 is well-known in the art (see for example, J. Rubio-Lightbourn, et al., Chem. Pharm. Bull., 21, 1854 (1973)).

In the final steps of the process for the preparation of 3-deoxy-1α-hydroxycholecalciferol 13, 1α-hydroxy-5,7-cholestadiene (11, R is hydrogen) dissolved in a suitable saturated aliphatic hydrocarbon, such as pentane, hexane and the like, or an ethereal solvent, such as ether, tetrahydrofuran and the like, is irradiated by means of a medium pressure mercury lamp equipped with a Corex glass filter under an inert atmosphere, such as nitrogen, helium and the like, at a temperature from about −40° to about 25° C. for about 8 minutes to afford 3-deoxy-1α-hydroxyprecholecalciferol 12

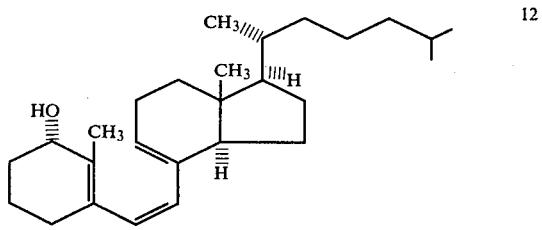

which is then isomerized to 3-deoxy-1α-hydroxycholecalciferol 13

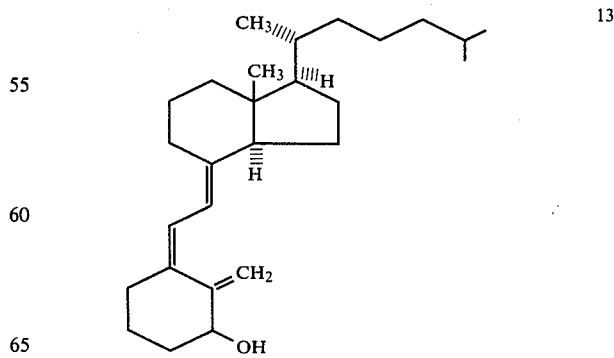

by heating the previtamin 12 in an inert organic solvent, such as dioxane, tetrahydrofuran and the like, under an inert atmosphere, such as nitrogen, helium and the like at about 75° C. for about 2 hours. The irradiation and isomerization steps follow paths well-trodden in the art. (see for example, Barton, et al., supra).

In the first step of the process of the present invention for the preparation of 3-deoxy-1α25-dihydroxycholecalciferol 13a, 1α,25-dihydroxycholesterol 14,

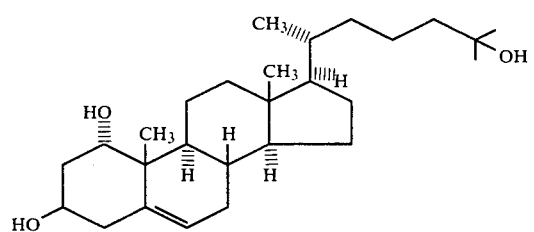

prepared from cholesterol 2 via 25-hydroxycholesterol 15

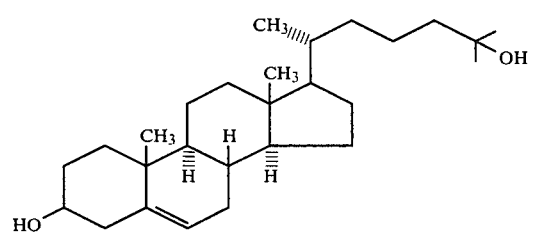

according to the procedures of Narwid, et al. (Helv. Chim. Acta., 57, 781 (1974) and Barton, et al. (J. Chem. Soc. Chem. Commun., 203 (1974), is selectively sulfonated to a compound of formula 16

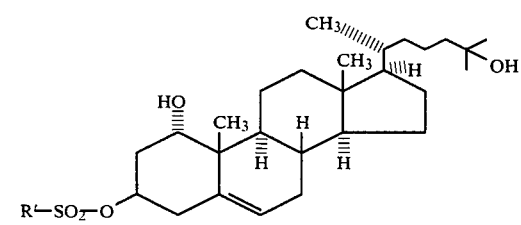

wherein R¹ is lower alkyl, phenyl or lower-alkylphenyl by the method for the conversion of 1α-hydroxycholesterol 6 to the sulfonate of formula 7.

The sulfonate of formula 16 is then reductively cleaved to 1α,25-dihydroxy-5-cholestene 17

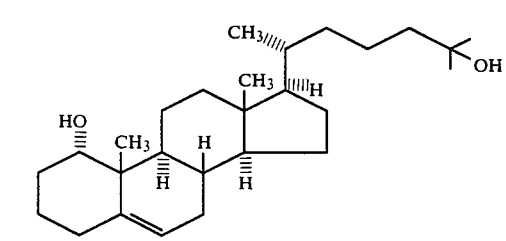

by the method described for the conversion of the 3β-sulfonate of formula 7 to 1α-hydroxy-5-cholestene 5.

The subsequent steps of the process for the preparation of 3-deoxy-1α,25-dihydroxycholecalciferol 13a follow those employed for the transformation of 1α-hydroxy-5-cholestene 5 to 3-deoxy-1α-hydroxycholecalciferol 13. Thus 1α,25-dihydroxy-5-cholestene 17 is acylated to the diacylate of formula 18

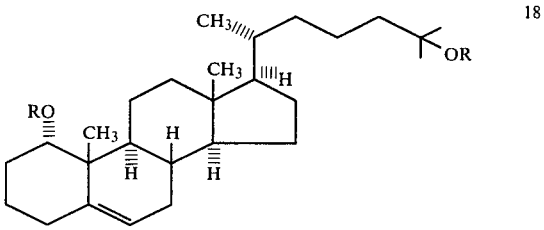

wherein R is lower alkanoyl by the method described for the acylation of 5 to compounds of formula 9 followed by bromination to a mixture of 7α- and 7β-bromo-1α,25-diacyloxy-5-cholestenes of formula 19

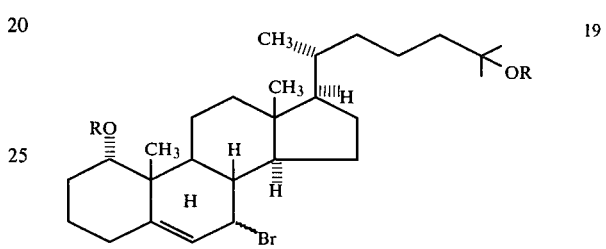

and dehydrobromination and hydrolysis to 1α,25-dihydroxycholesta-5,7-diene 20

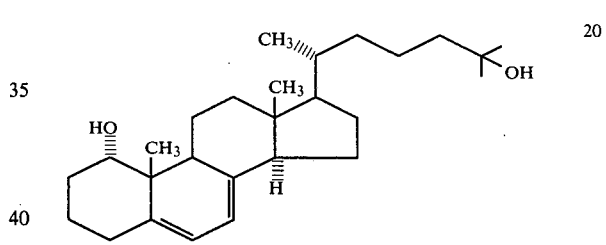

by the prodecure described for the conversion of acylates of formula 9 to 1α-hydroxy-5,7-cholestadiene of formula 11 by means of the intermediate mixture of 7α- and 7β-bromo-1α-acyloxy-5-cholestenes of formula 10.

The provitamin, 1α,25-dihydroxycholesta-5,7-diene 20 is then irradiated to the previtamin 21

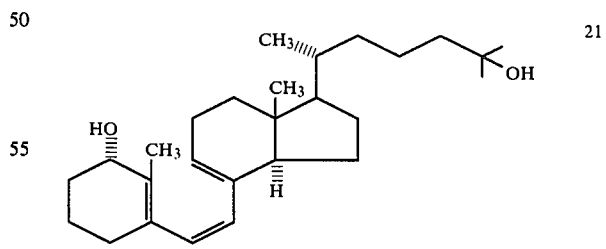

by the procedure described for the information of the previtamin 12 from the 5,7-cholestandiene 11 and isomerized to 3-deoxy-1α,25-dihydroxycholecalciferol 13a following the method used for the conversion of the previtamin 12 to 3-deoxy-1α-hydroxycholecalciferol 13.

The processes of the present invention are useful for the preparation of the potent selective intestinal calcium transport stimulators, 3-deoxy-1α-hydroxycholecalciferol 13 and 3-deoxy-1α,25-dihydroxycholecalciferol 13a.

4,6-Cholestadien-1α, 3β-diol 4, 1α-hydroxy-5-cholestene 5 and its lower alkanoly derivatives of formula 9, 1α-hydroxy-5,7-cholestadiene of formula 11 (wherein R is hydrogen) and its lower alkanoly derivatives of formula 11 (wherein R is lower alkanoly) and the lower alkyl-, phenyl and lower-alkylphenylsulfonates of 1α-hydroxycholesterol of formula 7 (wherein R' is lower alkyl, phenyl or lower-alkylphenyl) are useful intermediates for the preparation of 3-deoxy-1α-hydroxycholecalciferol.

1α,25-Dihydroxycholesteryl sulfonates of formula 16 (wherein R' is lower alkyl, phenyl or lower-alkylphenyl), 1α,25-dihydroxy-5-cholestene 17 and its lower alkanoyl detivatives of formula 18 (wherein R is lower alkanoyl) are useful intermediates for the preparation of 3-deoxy-1α,25-dihydroxycholecalciferol 13a.

3-Deoxy-1α-hydroxycholecalciferol 13 and 3-deoxy-1α,25-dihydroxycholecalciferol 13a stimulate intestinal calcium transport without significant concomitant mobilization of bone calcium release and thus are useful not only for the treatment of vitamin D deficiency and metabolic disorders in mammals where release of bone calcium is not detrimental, but also for the treatment of those disorders when release of bone calcium is undesirable. Bearing the 1α-hydroxyl group required for biological activity and introduced metabolically into vitamin D and its analogs in healthy subject by the kidney, 3-deoxy-1α-hydroxycholecalciferol and 3-deoxy-1α,25-dihydroxycholecalciferol 13a are also useful for the treatment of vitamin D diseases and metabolic disorders accociated with renal malfunction and uremic conditions.

In vitamin D deficient chicks, 3-deoxy-1α-hydroxycholecalciferol 13 stimulates calcium transport to a maximum level of about 7 times greater than that of rachitic control birds and elicits a response about 1.5 times greater than the response elicited by cholecalciferol or its potent, rapid-acting natural metabolite, 1α,25-dihydroxycholecalciferol. Maximum biological response is obtained at about 12 hours after administration of 3-deoxy-1α-hydroxycholecalciferol. Due to the presence of the 1α-hydroxyl group, the characteristic time lag of the 3-deoxy dervative 13 is about $\frac{1}{3}$-$\frac{1}{2}$ that of the present vitamin, cholecalciferol, and about the same as those of 1a 25-dihydroxychole-calciferol and 1α-hydroxycholecalciferol.

In vitamin D deficient chicks, 3-deoxy-1α,25-dihydroxycholecalciferol 13a stimulates calcium transport to a maximum level of about 5–7 times greater than that of rachitic control birds and elicts a response about equivalent to the response elicited by cholecalciferol or its potent, rapid-acting natural metabolite, 1α,25 -dihydroxycholecalciferol. Maximum biological response is obtained at about 12 hours after adminstration of 3-deoxy-1α,25-dihydroxycholecalciferol. Due to the presence of the 1α-hydroxyl group, the characteristic time lag of the 3-deoxy derivative 13a is about $\frac{1}{3}$ that of the parent vitamin, cholealciderol, and about the same as those of 1α,25-dihydroxycholecalciferol and 1 α-hydroxycholecalciderol.

Compared to 1α-hydroxycholecalciderol and 1 α,25-dihydroxycholecalciferol, 3 -deoxy-1α-hydroxycholecalciferol is virtually devoid of bone calcium mobilization activity in the in vivo system described in Example 13. While 1α,25-dihydroxycholecalciferol and 1α-hydroxycholecalciferol release significant amounts of calcium at a dose of $5 \times 10^{-5}$ μg/ml, 3-deoxy-1α-hydroxycholecalciferol does not significantly mobilize bone calcium at $5 \times 10^{-a}$ μg/ml, i.e., 3-deoxy-1α-hydroxycholecalciferol is about 10,000 times less active than the metabolites. 3-Deoxy-1α,25 -dihydroxycholecalciferol is about 1/50 as active as 1α,25-dihydroxycholecalciferol.

3-Deoxy-1α-hydroxycholecalciferol and 3-deoxy-1α,25-dihydroxycholecalciferol may be formulated with various conventional inert organic and inorganic pharmaceutical carriers suitable for parenteral or enteral administration such as, for example, water, gelatin, lactose, starch, magnesium sternate, talc, vegetable and fish liver oil, gums and the like. 3-Deoxy-1α-hydroxycholecalciferol can be administered in conventional pharmaceutical forms such as solid forms, for example, tables, dragees, capsules, suppositories or the like, or in liquid forms such as solutions, suspension, suppositories or the like. The pharmaceutical compositions containing 3-deoxy-1α-hydroxycholecalciferol and 3-deoxy-1α,25-dihydroxycholecalciferol can be subjected to conventional pharmaceutical processes such as sterilization, and can contain conventional pharmaceutical excipients such as preservatives, stabilizing agents, emulsifying agents, salts for adjusting osmotic pressure or buffers. The pharmaceutical compositions can also contain other therapeutically valuable substances.

A suitable pharmaceutical dosage unit might contain about 10 to 1000 μg of 3-deoxy-1α-hydroxycholecalciferol and 1-100 μg of 3-deoxy-1α,25-dihydroxycholecalciferol.

Suitable parenteral dosage regimens in mammals comprise from about 1 μg/kg to about 25 μg/kg per day. For any particular subject, the specific dosage regimen should be adjusted according to the disorder being treated, the individual needs of the patient and the professional judgments of those administering or supervising the administration of 3-deoxy-1α-hyroxycholecalciferol or 3-deoxy-1α,25-dihydroxycholecalciferol. The dosages set forth herein are exemplary. They do not to any extent limit the scope or practice of this invention.

EXAMPLES

The following examples are illustrative only of the invention and are not to be construed as limiting the invention in any manner.

EXAMPLE 1

1,4,6-Cholestatrien-3-one (3). 1,4,6-cholestatrien-3 one was prepared in 56% yield from cholesterol, 2,3-dichloro-5,6-dicyano-1,4-benzoquinone and dioxane by the procedure of A. B. Turner J. Chem. Soc. C, 2568 (1968).

EXAMPLE 2

1α,2α-Oxido-4,6-cholestanien-3-one (1). 1α,2α-Oxido-4,6-cholestandien-3-one was prepared in 72% yield 1,4,6-cholestatrien- 3-ones, aqueous 30% hydrogen peroxide, 15% sodium hydroxide solution and methanol by the procedure of B. Pele and E. Kodicek, J. Chem. Soc. C, 1568 (1971).

EXAMPLE 3

4,6-Cholestandien-1α,3β-diol (4). a solution of 1α,2α-oxide-4,6-cholestadien-3-one (1, 5.0 g, 0.013 mole) in anhydrous ether (200 ml) was heated under reflux with lithium aluminum hydride (2.5 g, 0.066 mole) under anhydrous conditions for 5 hours. The reaction mixture was cooled in an ice-bath and water (2.5 ml), 15% sodium hydroxide solution, and water (7.5 ml) were added succesively to the well-stirred reaction mixture. The precipitate was collected on a filter and the filter cake was washed with ether. The filtrate was evaporated under vacuum and the residue was chromatographed on Woelm neutral alumina, grade III (150 g). The material (3.8 g) eluted with benzene-ether (2:1) was recrystallized from acctone-methanol to give the diol 4 as needles (3.25 g, 62% yield), mp 120°–121° C.

Anal. Calc'd for $C_{27}H_{44}O_2$: C, 80.94; H, 11.07. Found C, 80.81; H, 11.21.

EXAMPLE 4

1α-Hydroxy-5-cholestene (5). A three-necked standard taper round-bottom flask equipped with a mechanical stirrer, dry ice condenser, a nitrogen inlet and an ammonia inlet was thoroughly dried, flushed with nitrogen, cooled in a dry ice-acetone bath and charged with ammonia (60 ml). Lithium (0.4 g, 0.06 mole) was added portionwise under an atmosphere of nitrogen with stirring. A solution of 4,6-cholestadien-1α,3β-diol (4, 0.518 g, 1.29 mmoles) in freshly distilled tetrahydrofuran (60 ml) was added and, after removal of the cooling bath, the reaction mixture was stirred for 3 hours. Ammonium chloride (ca 0.5 g) was added and after stirring for 1 hour, saturated ammonium chloride solution was added. The ammonia was allowed to evaporate. Water was added o the residue and the solution was extracted with ether. The combined organic extracts were washed with water, dried over anhydrous sodium sulfate, filtered and the filtrate was evaporated under vacuum. Filtration of the residual solid (0.509 g) dissolved in low boiling petroleum ether through a column of silica gel gave 0.3 g (60%) of carbinol 5.

For analysis, a sample was purified by preparative thin-layer chromatography on silica gel followed by recrystallization from 95% ethanol. The carbinol 5 had mp 102°–103° C.

Anal. Calc'd for $C_{27}H_{46}O$: C, 83.87; H, 11.99. Found: C, 83.71; H, 12.34.

EXAMPLE 5

1α-Hydroxycholesterol (6). 1α,2α-Oxido-4,6-cholestadien-3-one (1, 3.0 g, 7.6 mmoles) in tetrahydrofuran (100 ml) was treated with lithium (4.0 g, 0.58 mole) for 3 hours by the procedure described above for the reduction of 4. Ammonium chloride (25 g) was added to the reaction mixture, with stirring, and after one hour, saturated ammonium chloride solution was added cautiously with vigorous stirring. The ammonia was allowed to evaporate. Water was added and the solution was extracted with ether. The combined ethereal extracts were washed with water, dried over anhydrous sodium sulfate, fltered and the filtrate was evaporated under vacuum. Chromatography of the residue (3.05 g) over alumina (Woelm neutral, grade III, 50% ethyl acetate-ethanol) followed by recrystallization from acetone gave 1.5 g (49%) of the carbinol 6, mp 156°–157° C.

EXAMPLE 6

1α-Hydroxycholesteryl Tosylate (7, R' is 4-methylphenyl).

A solution of 1α-hydroxycholesterol (6, 1.0 g, 2.5 mmoles), p-toluenesulfonyl chloride (1.0 g, 5.2 mmoles) and anhydrous pyridine (5 ml) was allowed ot stand overnight in a freezer having a temperature less than 0° C. Cold water and ether were added to the reaction mixture. The phases were separated and the ethereal phase was washed with cold water, dried over anhydrous sodium sulfate, filtered and the filtrate was evaporated. the crystalline residue (1.35 g) was suitable without further purification for use in the subsequent steps.

For analysis, a sample was recrystallized from acetone-low boiling petroleum ether. The analytical sample has mp 147° C. (dec.).

Anal. Calc'd for $C_{35}H_{52}O_4S$: C, 73.33; H, 9.41. Found: C, 73.02; H, 9.48.

EXAMPLE 7

1α-Hydroxy-5-cholestene (5). A solution of 1α-hydroxycholesteryl tosylate (7, R' is 4-methylphenyl, 1.35 g) in anhydrous ether (80 ml) was heated under reflux with lithium aluminum hydride (0.098 g, 23.9 mmoles) under anhydrous conditions for 5 hours. Work-up of the reaction mixture as described in the above procedure for the preparation of 4,6-cholestadien-1α,3β-diol 4 followed by chromategraphy of the crude carbinol on silica gel (25 g) using low boiling petroleum ether-benzene as the eluent gave 705 mg (72% yield based on 1α-hydroxycholesterol 6) of 5.

EXAMPLE 8

1α-Acetoxy-5-cholestene (9, R is acetyl). A solution of 1α-hydroxy-5-cholestene (5, 1.5 g, 3.9mmoles), acetic anhydride (5 ml), pyridine (5 ml) and 4-dimethylaminopyridine (1.0 g) was allowed to stand at room temperature overnight. Cold water and ether were added to the reaction mixture. The phases were separated and the ethereal extract was washed with cold dilute hydrochloric acid, water and sodium bicarbonate solution. The organic extract was dried over anhydrous sodium sulfate, filtered and the filtrate was evaporated under reduced pressure. The residue was dissolved in benzene and filtered through a column of silica gel. Evaporation of the cluent followed by recrystallization of the residue from benzene gave 1.40 g (85% yield) of the acetoxy derivative (9, R is acetyl) as needles, mp 69°–70° C.

Anal. Calc'd for $C_{29}H_{48}O_2$: C, 81.25; H, 11.29. Found: C, 81.51; H, 11.20.

EXAMPLE 9

1α-Acetoxy-5,7-cholestadiene (11, R is acetyl). To a magnetically stirred solution of 1α-acetoxy-5-cholestene (9, R is acetyl, 0.415 g, 0.97 mmole) in 1:1 benzene-hexane (90 ml) heated under reflux under anhydrous conditions was added 1,3-dibromo-5, 5-dimethylhydantoin (0.145 g, 0.51 mmole) in one portion. The reaction mixture was heated under reflux for 15 minutes and then cooled in an ice-bath. The precipitate was collected on a filter and washed with cold low boiling petroleum ether. The combined filtrates were evaporated to dryness at room temperature under vacuum to give a yellow residual syrup.

The yellow residual syrup was dissolved in xylene (50 ml) and the solution was added dropwise, with stirring, to a refluxing solution of trimethylphosphite (1.5 ml) in xylene (25 ml). After the addition was complete (ca ½ hour), the reaction mixture was heated under reflux for one hour, and after cooling, the mixture was evaporated to dryness at water pump vacuum and then under high vacuum.

The residue was dissolved in a small volume of low boiling petroleum ether and was chromatographed on 10% silver nitrate impregnated silica gel (15 g) using ether-low boiling petroleum ether (0%, 200 ml; 2%, 350 ml; 4%, 500 ml; 10%, 100 ml) as the eluents. Fourteen milliliter fractions were collected. Fractions 52–75 contained mainly 1α-acetoxy-5,7-cholestadiene as determined by ultraviolet spectroscopy. These fractions were pooled and evaporated under vacuum. The residue (55 mg) was chromatographed on silica gel (8 g) using ether-low boiling petroleum ether (0%, 60 ml; 2%, 90 ml; 6%, 30 ml) as the eluents. Thirteen milliliter fractions were collected and evaporation of fraction 4 under reduced pressure gave 45 mg (11% yield) of 1α-acetoxy-5,7-cholestadiene, mp 105°–106° C.

In a subsequent experiment, further purification by preparative thin-layer chromatography followed by recrystallization from ethanol afforded the acetate as colorless needles, mp 108°–109° C.

EXAMPLE 10

1α-Hydroxy-5,7-cholestadiene (11, R is hydrogen). A solution of 1α-acetoxy-5,7-cholestadiene (11, R is acetyl, 8.3 mg) and 5% methanolic potassium hydroxide (10 ml) was allowed to stand at room temperature under an atmosphere of nitrogen overnight. Work-up of the reaction mixture in the usual way gave 1α-hydroxy-5,7-cholestadiene.

EXAMPLE 11

3-Deoxy-1α-hydroxycholecalciferol (13). 1α-Hydroxy-5,7-cholestadiene (11, R is hydrogen) from the above experiment was dissolved in ether and irradiated with a 100 watt medium pressure mercury lamp equipped with a Corex glass filter under an atmosphere of nitrogen for 8 minutes by the method of Barton, et al., J. Am. Chem. Soc., 95, 2748 (1973). The crude irradiation product was chromatographed on silica gel (12 g) using low boiling petroleum ether (100 ml), 2% ether-low boiling petroleum ether (100 ml), 5% ether-low boiling petroleum ether (100 ml), 8% ether-low boiling petroleum ether (200 ml) and 10% ether-low boiling petroleum ether (100 ml) as the eluents. Ten milliliter fractions were collected. Fractions 36–39, the ultraviolet spectra of which showed maxima at 260 nm and minima at 230 nm, were combined and evaporated to afford 3-deoxy-1α-hydroxyprecholecalciferol (12).

The 3-deoxy-1α-hydroxyprecholecalciferol from the preceding experiment was dissolved in the required volume of iso-octane and the solution was heated at 75° C. for 2.15 hours under a nitrogen atmosphere according to the procedure of Barton, et al., supra. The solvent was evaporated and the residue was chromatographed on silica gel (10 g) using low boiling petroleum ether (150 ml) and ether-low boiling petroleum ether (3%, 150 ml; 5%, 150 ml; 8%, 100 ml) as the eluents. Ten milliliter fractions were collected. Fractions 37–40, the ultraviolet spectra of which showed maxima at 262 nm and minima at 227 nm, were combined and evaporated to give 0.63 mg of 3-deoxy-1α-hydroxycholecalciferol. The thin-layer chromatography of the vitamin showed one spot. The vitamin exhibited the expected mass spectrum having the calculated molecular ion.

EXAMPLE 12

Determination of Bone Calcium Mobilization in vitro.

$^{45}$Calcium chloride (200 µCi) was administered to 17-day pregnant rats, and after 48 hours, the rats were sacrificed and the fetuses were separated. Fetal radii and ulnae were isolated and cultured in Biggers-Gwatkin-Heyner medium. Paired radii and ulnae were employed. One bone was treated with a solution of the vitamin $D_3$ derivative in 95% ethanol and its pair was used as the control. The bones were cultured in a carbon dioxide incubator for 72 hours. At the end of the culture period, aliquots of the media were collected and the released $^{45}$calcium was counted.

The effectiveness of the vitamin $D_3$ derivative in promoting bone calcium release is expressed as the ratio of the number of counts per minute (T) of released $^{45}$calcium from the treated bone to the number of counts per minute (C) of released $^{45}$calcium from it paired control. A T/C ratio greater than 1 indicates a significant release of bone calcium in response to the vitamin $D_3$ derivative.

| Mobilization of Bone Calcium | | |
| --- | --- | --- |
| Compound | Dose (µg/ml) | T/C ± S.E. |
| 1α,25-(OH)$_2$-D$_3$ | 2 × 10$^{-5}$ | 1.62 ± 0.17 |
|  | 5 × 10$^{-5}$ | 1.93 ± 0.12 |
| 1α-OH-D$_3$ | 5 × 10$^{-3}$ | 1.75 ± 0.20 |
| 3-D-1α-OH-D$_3$ | 0.5 | 0.83 ± 0.05 |
|  | 1.0 | 1.29 ± 0.20 |
| 3-D-1α,25-(OH)$_2$-D$_3$ | 0.5 × 10$^{-3}$ | 1.66 ± 0.04 |
|  | 1.0 × 10$^{-3}$ | 1.98 ± 0.13 |
|  | 5.0 × 10$^{-3}$ | 2.21 ± 0.27 |

Four bone pairs were used for each determination.
1α, 25-Dihydroxycholecalciferol (1α,25-(OH)$_2$-D$_3$)
1α-Hydroxycholecalciferol (1α-OH-D$_3$)
3-Deoxy-1α-hydroxycholecalciferol (3-D-1α-OH-D$_3$)
3-Deoxy-1α,25-dihydroxycholecalciferol (3-D-1α,25-(OH)$_2$D$_3$
Standard error of the mean (S.E.)

EXAMPLE 13

Determination of Intestinal Calcium Transport in vivo.[a]

Chicks were maintained on a rachitogenic diet for 3 weeks. The vitamin $D_3$ derivative dissolved in 0.2 ml of 1:1-1,2-propandiol and ethanol was administered interperitoneally. After 24 hours, the duodenal loop was lifted out, 0.2 ml of a solution of $^{45}$calcium chloride (2 µCi) in 95% ethanol was placed in the loop and the loop was returned to the cavity. Thirty minutes thereafter, the chicks were sacrificed by decapitation, the blood was collected, the serum was separated and the amount of $^{45}$calcium absorbed from the duodenal loop was determined radiographically.

| Stimulation of Intestinal Calcium Transport[a] | | | |
| --- | --- | --- | --- |
| Compound | Administered dose | Time of assay after dosing | Intestinal Calcium[b] Absorption (plasma $^{45}$Ca$^{2+}$) | Relative Enhancement over control |
|  | (nmoles) | (hours) | cpm/0.20ml ± SEM |  |

| -continued | | | | |
|---|---|---|---|---|
| Stimulation of Intestinal Calcium Transport[a] | | | | |
| Control | None | — | 430 ± 15 | 1.0 |
| $D_3$ | 1.3 | 10 | 620 ± 18 | 1.4 |
| $D_3$ | 1.3 | 24 | 1360 ± 40* | 3.2 |
| $D_3$ | 2.6 | 24 | 2060 ± 65* | 4.8 |
| $D_3$ | 26.0 | 24 | 1730 ± 72* | 4.0 |
| $1\alpha,25\text{-}(OH)_2\text{-}D_3$ | 0.6 | 10 | 1950 ± 68* | 4.5 |
| $1\alpha,25\text{-}(OH)_2\text{-}D_3$ | 0.6 | 24 | 780 ± 21 | 1.8 |
| $1\alpha\text{-}OH\text{-}D_3$ | 1.6 | 10 | 2010 ± 52* | 4.7 |
| $1\alpha\text{-}OH\text{-}D_3$ | 0.8 | 24 | 1920 ± 64* | 4.5 |
| $3\text{-}D\text{-}1\alpha\text{-}OH\text{-}D_3$ | 26.0 | 9 | 1047 ± 67* | 2.4 |
| $3\text{-}D\text{-}1\alpha\text{-}D_3$ | 26.0 | 12 | 3000 ± 220* | 7.0 |
| $3\text{-}D\text{-}1\alpha\text{-}OH\text{-}D_3$ | 26.0 | 24 | 1930 ± 95* | 4.5 |
| $3\text{-}D\text{-}1\alpha\text{-}OH\text{-}D_3$ | 5.2 | 24 | 1880 ± 96* | 4.4 |
| | (nmoles) | (hours) | (cpm/0.2ml ± SEM) | |
| Control (-D) | none | — | 310 ± 15 | 1.0 |
| $1\alpha,25\text{-}(OH)_2\text{-}D_3$ | 6.5 | 8 | 1100 ± 30* | 3.5 |
| $1\alpha,25\text{-}(OH)_2\text{-}D_3$ | 6.5 | 12 | 1200 ± 60* | 3.9 |
| $1\alpha,25\text{-}(OH)_2\text{-}D_3$ | 6.5 | 16 | 1230 ± 40* | 4.0 |
| $1\alpha,25\text{-}(OH)_2\text{-}D_3$ | 6.5 | 36 | 580 ± 15 | 1.9 |
| $1\alpha,25\text{-}(OH)_2\text{-}D_3$ | 0.26 | 12 | 1000 ± 40* | 3.2 |
| $1\alpha,25\text{-}(OH)_2\text{-}D_3$ | 1.30 | 12 | 1010 ± 25* | 3.2 |
| $3D\text{-}1\alpha,25\text{-}(OH)_2\text{-}D_3$ | 6.5 | 8 | 750 ± 30* | 2.4 |
| $3D\text{-}1\alpha,25\text{-}(OH)_2\text{-}D_3$ | 6.5 | 12 | 800 ± 20* | 2.4 |
| $3D\text{-}1\alpha,25\text{-}(OH)_2\text{-}D_3$ | 6.5 | 16 | 1060 ± 40* | 3.4 |
| $3D\text{-}1\alpha,25\text{-}(OH)_2\text{-}D_3$ | 6.5 | 36 | 400 ± 12 | 1.3 |
| $3D\text{-}1\alpha,25\text{-}(OH)_2\text{-}D_3$ | 0.26 | 16 | 370 ± 20 | 1.2 |

[a]The steroids were administered intraperitoneally in 0.20 ml of 1,2-propanediol: ethanol, 1:1. At the indicated time an assay of intestinal calcium transport was carried out exactly as described by Hibberd and Morman (10). For this assay 4.0 mg of $^{40}Ca^{2+}$ & $^{45}Ca^{2+}$ (2 µCi) are placed in a duodenal loop, in vivo. Thirty minutes later the appearance of $^{45}Ca^{2+}$ is measured in the blood. Each number is the average ± SEM for groups of 6–8 birds.
[b]Values indicated by * are significantly different from the control (-D) at P < 0.01.
Cholecalciferol ($D_3$)
1α,25-Dihydroxycholecalciferol (1α,25-OH)$_2$-$D_3$)
1α-Hydroxycholecalciferol (1α-OH-$D_3$)
3-Deoxy-1α-hydroxycholecalciferol (3-D-1α-OH-$D_3$)

EXAMPLE 14

1α,25-Dihydroxycholesterol Tosylate (16, R' is 4-methylphenyl). A solution of 1α,25-dihydroxycholesterol (15, 0.5 g, 1.19 mole), p-toluenesulfonyl chloride (0.575 g, 3 mmole) and anhydrous pyridine (5 ml) was allowed to stand in a freezer having a temperature less than 0° C. for 30 hours. Work-up of the reaction mixture as described in Example 6 followed by recrystallization from acetone-petroleum ether afforded 0.552 g (81%) of the tosylate (16, R' is 4-methylphenyl), mp 138°–139° C.

EXAMPLE 15

1α,25-Dihydroxy-5-cholestene (17). A solution of 1α,25-dihydroxycholesteryl tosylate (16, R' is 4-methylphenyl, 0.570 g, 1.00 mmole), lithium aluminum hydride (1.033 g, 27 mmole) and anhydrous ether (150 ml) was heated under reflux for 20 hours. Work-up of the reaction mixture by the procedure described in Example 3 followed by chromatography of the crude reaction mixture on silica gel using low boiling petroleum ether-benzene as the eluent gave 0.282 g (70%) of the diol 17, mp 127°–128° C. and 135°–136° C.

EXAMPLE 16

1α,25-Diacetoxy-5-cholestene (19, R is acetyl). A solution of 1α,25-dihydroxy-5-cholestene (17, 0.195 g, 0.484 mmole), acetic anhydride (4 ml) and anhydrous pyridine (4 ml) was heated at 90° C. for 24 hours. Work-up by the procedure described in Example 8 followed by filtration of a solution of the residue in 2% acetone-benzene through silica gel and recrystallization from methanol gave the diacetate 20, mp 106°–107° C.

EXAMPLE 17

1α,25-Dihydroxy-5,7-cholestadiene (20). 1α,25-Diacetoxy-5-cholestene (19, R is acetyl, 0.223 g, 0.46 mmole) in 1:1 benzenehexane was treated with 1,3-dibromo-5,5-dimethylhydantoin (0.675 g, 0.23 mmole) as described in Example 9.

The crude bromo compound in xylene (10 ml) was added dropwise to boiling s-collidine (14 ml) under an atmosphere of nitrogen. After the addition was complete, the reaction mixture was heated under reflux for 30 minutes, allowed to cool, worked up in the usual manner and chromatographed on 10% silver nitrate impregnated silica gel (linear gradient between equal volumes of petroleum ether and 1:1 ether-petroleum ether). Fractions showing ultraviolet absorption maxima at 280 nm and 312 nm were pooled and concentrated.

A solution of the residue, 5% methanolic potassium hydroxide (45 ml) was allowed to stand at 25° C. for 12 hours. Work-up of the reaction mixture in the usual way followed by chromatography of the residue on silica gel (linear gradient between equal volumes of petroleum ether and ether) gave 17 mg of the dihydroxy diene 20, pure by thin-layer chromatography as detected by ultraviolet irradiation.

The product had mp 151°–152° C. after recrystallization from methanol-water.

EXAMPLE 18

3-Deoxy-1α,25-dihydroxycholecalciferol (13a ). 1α,25-Dihydroxy-5,7-cholestadiene (12 mg) in ether was irradiated with a 100 watt medium pressure mercury lamp equipped with a Corex glass filter under an atmosphere of nitrogen with ice cooling for 8 minutes by the method described in Example 11 to give 3-deoxy-1α,25dihydroxyprecholecalciferol (21).

The 3-deoxy-1α,25-dihydroxyprecholecalciferol (21) from the above was isomerized by heating in iso-octane at 75° C. for 2.25 hours according to the procedure of Example 11. Chromatography of the residue twice on silver nitrate impregnated with silica gel as in Example 17 gave 1.4 mg (12%) of 3-deoxy-1α,25-dihydroxycholecalciferol (13a), homogeneous by thin-layer chromatography. 3-Deoxy-1α,25-dihydroxycholecalciferol showed the expected ultraviolet absorption maximum at 263 nm and minimum at 288 nm. It also exhibited a mass spectrum having the calculated molecular ion.

We claim:

1. A compound of the formula

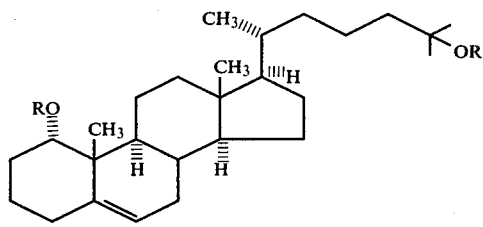

wherein R is hydrogen or lower alkanoyl.

2. The compound of claim 1 wherein R is hydrogen.
3. The compound of claim 1 wherein R is lower alkanoyl.
4. The compound of claim 1 wherein R is acetyl.
5. 1α,25-Dihydroxycholesta-5,7-diene.
6. 3-Deoxy-1α,25-dihydroxyprecholecalciferol.
7. 3-Deoxy-1α,25-dihydroxycholecalciferol.
8. A process for the preparation of

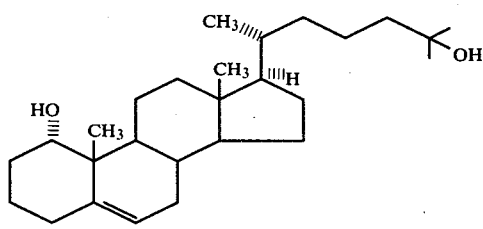

which comprises
(a) treating

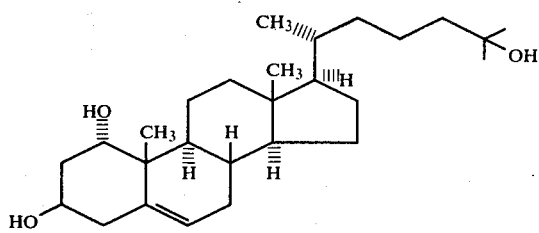

with a sulfonyl halide of the formula

wherein R' is lower alkyl, phenyl or lower-alkyl-phenyl and X is chloro or bromo
in the presence of an acid-acceptor to form a sulfonate of the formula

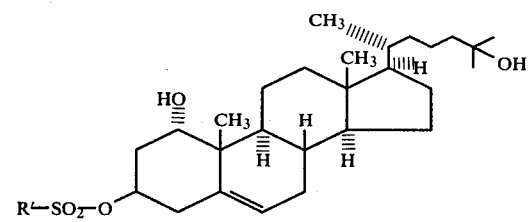

wherein R' is as above and
(b) treating the sulfonate with an alkali metal aluminum hydride in an inert solvent.

9. The process of claim 8 wherein R' is 4-tolyl.
10. The process of claim 8 wherein the acid-acceptor is an organic base.
11. The process of claim 8 wherein the organic base is pyridine.
12. The process of claim 8 wherein the alkali metal aluminum hydride is lithium aluminum hydride.
13. The process of claim 8 wherein the inert organic solvent is an ethereal solvent.
14. The process of claim 8 wherein the ethereal solvent is ether.

* * * * *